United States Patent [19]

Oshima et al.

[11] Patent Number: 5,316,914
[45] Date of Patent: May 31, 1994

[54] METHOD FOR DETERMINING HUMAN COLLAGEN PEPTIDES BY WAY OF ENZYME IMMUNOASSAY

[75] Inventors: Akira Oshima, Wakayama; Kazushi Iwata, Takaoka; Yasuteru Muragaki, Wakayama; Yasuo Bai, Sakai; Eisaku Matsumoto; Satoshi Miyamoto, both of Wakayama, all of Japan

[73] Assignee: Fuji Yakuhin Kogyo Kabushiki Kaisha, Toyama, Japan

[21] Appl. No.: 831,645

[22] Filed: Feb. 7, 1992

Related U.S. Application Data

[63] Continuation of Ser. No. 488,440, Feb. 27, 1990, abandoned, which is a continuation of Ser. No. 022,370, Mar. 5, 1987, abandoned.

[30] Foreign Application Priority Data

Sep. 4, 1986 [JP] Japan .................. 61-206862

[51] Int. Cl.⁵ ................. G01N 33/543; G01N 33/576; G01N 33/577
[52] U.S. Cl. .................................. 435/7.94; 436/578; 436/548
[58] Field of Search ................. 435/7.94; 436/578, 548

[56] References Cited

U.S. PATENT DOCUMENTS

| | | | |
|---|---|---|---|
| 4,312,853 | 1/1982 | Timpl | 436/541 |
| 4,376,110 | 3/1983 | David et al. | 435/7 |
| 4,504,587 | 3/1985 | Timpl et al. | 436/538 |
| 4,628,027 | 12/1986 | Gay | 436/506 |

FOREIGN PATENT DOCUMENTS 0204726 10/1985 Japan .
8500663 2/1985 PCT Int'l Appl. .

OTHER PUBLICATIONS

T. S. Baker et al., in W. P. Collins (Ed.) *Alternative Immunoassays*, John Wiley & Sons Ltd., Chichester, U.K., 1985, pp. 59–76.
Rohde et al., Eur. J. Clin. Invest, 9, 451–459, (1979).
Hales et al., Meth. Enzymol., 20, 334–355, 1980.
Oshima et al., Chem. Abs., 109, Abstr. No. 166876j, 1988.
Clark et al., In Maggio (Ed.), *Enzyme-Immunoassay*, CRC Press Inc., Boca Raton, Fl., 1980, pp. 167–179.

*Primary Examiner*—David Saunders
*Attorney, Agent, or Firm*—Birch, Stewart, Kolasch & Birch

[57] ABSTRACT

A method for determining human type III, IV and VI collagen peptides by way of enzyme immunoassay according to the sandwich technique using a monoclonal antibody and a polyclonal antibody each to the human type III, IV or VI collagen peptide, characterized in that the monoclonal antibody to the collagen peptide is used as an antibody to be coated onto a solid phase and/or an antibody to be labeled with an enzyme. Also disclosed is a sandwich technique using two different monoclonal antibodies. This method can be carried out with a smaller amount of samples in a simple manner to obtain a precise result and is thus useful for diagnosis of hepatic diseases.

3 Claims, 4 Drawing Sheets

METHOD FOR DETERMINING HUMAN COLLAGEN PEPTIDES BY WAY OF ENZYME IMMUNOASSAY

This application is a continuation of application Ser. No. 07/488,440 filed on Feb. 27, 1990 and now abandoned, which is a Rule 62 continuation application of Ser. No. 07/022,370 filed on Mar. 5, 1987 and now abandoned, the entire contents of which are incorporated herein by reference.

BACKGROUND OF THE INVENTION

1. Field of the Invention:

This invention relates to a method for determining human type III, IV and VI collagen peptides, which is useful for easy diagnosis of hepatic diseases. More particularly, this invention relates to a method for quantitative determination of the human type III, IV and VI collagen peptides by way of enzyme immunoassay based on the so-called sandwich method (technique) wherein specific monoclonal and polyclonal antibodies to the human type III, IV and VI collagen peptides are used.

2. Description of the Prior Art:

A radioimmunoassay for the measurement of the human type III procollagen N-terminal peptide in human blood using a polyclonal antibody was already reported, for example, in Rohde et al., Eur. J. Clin. Invest. 9, 451–459, (1979).

However, a method for the determination of the human type III, IV and VI collagens themselves in blood has not yet been known, chiefly for the reason that the structure of collagens is not so significantly different among animal species as to make it easy to produce an antibody for assay from other animals and that the solubility of collagens in blood is too poor to measure the concentration of collagens in blood. If human collagens per se in blood can be measured exactly, it will greatly contribute to convenient and easy diagnosis of hepatic diseases. Consequently, there is a great demand for developing a new method for effectively and precisely determining human collagen peptides in a simple manner, especially in the field of diagnosis of hepatic diseases.

BRIEF SUMMARY OF THE INVENTION

Accordingly, it is an object of the present invention to provide a new method for determining human type III, IV and VI collagen peptides in a simple manner.

It is another object of the present invention to provide a method for the enzyme immunoassay of human type III, IV and VI collagen peptides applicable to diagnosis of hepatic diseases.

It is still another object of the present invention to provide a method for effectively and precisely determining human type III, IV and VI collagen peptides by way of enzyme immunoassay based on the sandwich technique with a specific monoclonal antibody to these collagen peptides.

Other objects, features and advantages of the present invention will become apparent as the description proceeds.

DETAILED DESCRIPTION OF THE INVENTION

As a result of extensive research made by the present inventors for developing a new simple method for determining the human type III, IV and VI collagen peptides in a specific manner, it has now been found that a precise and rapid determination of the human type III, IV and VI collagen peptides can be carried out with a small amount of samples by way of enzyme immunoassay according to the sandwich technique using a specific monoclonal antibody to each collagen peptide.

In accordance with the present invention, there is provided a method for determining human type III, IV and VI collagen peptides by way of enzyme immunoassay according to the sandwich technique using a monoclonal antibody and a polyclonal antibody each to the human type III, IV or VI collagen peptide, characterized in that the monoclonal antibody to the human type III, IV or VI collagen peptides is used as at least either of the antibodies to be coated onto a solid phase and to be labeled with an enzyme.

The specific monoclonal antibody employed in the method of this invention is an anti-human collagen peptide monoclonal antibody of IgG, IgA and IgM classes, which is obtained by immunizing an animal such as a mouse with human collagen peptides to form a hybridoma from anti-human collagen peptide monoclonal antibody-producing cells of the animal and myeloma cells, cloning the hybridoma and thereafter selecting and cultivating clones capable of producing an anti-human collagen peptide monoclonal antibody having reactivity with any of the human type III, IV and VI collagen peptides. This monoclonal antibody can be purified, if necessary, according to a conventional purifying method by fractionation with a sulfate such as ammonium sulfate followed by column chromatography with DEAE-Sephacel (Pharmacia Fine Chemicals) equilibrated with a buffer of a particular pH value.

The polyclonal antibody employed in the method of this invention is obtained by immunizing an animal such as a rabbit with the human collagen peptides, taking blood from the immunized animal and purifying the resultant anti-serum.

Employed as the antibody to be labeled with an enzyme, especially with a peroxidase in the method of this invention is an IgG fraction obtainable by the fractionation of a material containing antibodies with ammonium sulfate or sodium sulfate and the subsequent purification on a DEAE-cellulose such as DEAE-Sephacel column. In case of the polyclonal antibody, it is preferred to carry out further purification on a Sepharose 4B affinity column because this would enhance the specificity. It is also possible to use F(ab')$_2$ obtainable by digestion with pepsin or its reduced product Fab'. Thus, the present invention includes such an embodiment wherein the monoclonal and polyclonal antibodies used in the method of this invention may be their specific binding sites F(ab')$_2$ or Fab' as such.

The solid phase to be coated with the monoclonal or polyclonal antibody should normally be inert to all the substances used for the antigen-antibody reaction including a liquid vehicle and is selected from a wide variety of inorganic and organic inert carrier materials such as glass, ceramics and resinous materials in the form of a plate or sphere. Such solid phase should be homogeneous in quality and identical in size, or otherwise, the quantity of the monoclonal or polyclonal antibody coated on the individual solid phase fluctuates, thus resulting in an inaccurate result of measurements. Because of the ease in processing, organic resinous materials such as polystyrene, polyvinyl resin, polyamide resin in the form of a plate or sphere is preferable, with polystyrene balls and polyvinyl chloride plates being most preferable. A preferable example of the enzymes utilizable for the labeling of the monoclonal antibody is a peroxidase such as one derived from horse raddish.

Various kinds of buffer solutions can be used for the immunoassay of the present invention to provide a definite pH value desirable in the system. A buffer substance used for this purpose is selected from various known compounds having a buffering action, according to the conditions required in the system. Preferable examples of the buffer substances include phosphates, tris-HCl, acetates and amino acids. These substances are used with an acid or sodium chloride at a concentration desired in the system. The operations for the immunization, chromatography, equilibration, fractionation and spectrophotometry in the method of this invention can be carried out according to the methods known per se for these purposes.

Accordingly, the method of the present invention is featured by a solid phase enzyme immunoassay which is unique in using monoclonal antibodies to the human type III, IV and VI collagen peptides as an antibody to be coated onto a solid phase or to be labeled with an enzyme.

Our recent immunological tests have revealed that a significant increase in the human collagen peptide level is observed in tissue or blood of patients suffering from liver fibrosis caused by hepatic diseases such as chronic hepatitis and liver cirrhosis.

As will be shown in the accompanied FIGS. 2, 3 and 4, the human type III, IV and VI collagen peptides levels in sera from patients with liver cirrhosis as measured in accordance with the method this invention are significantly higher than those of sera from healthy normal subjects. According to the present invention, the measurement of the collagen peptide levels in blood is carried out in a simple manner and enables foreknowing hepatic diseases, especially liver fibrosis, without relying on biopsy which is burdensome on patients. We have confirmed that fibrosis of hepatic tissues cannot be determined by the conventional liver function tests relying on measurement of the activity of ZTT (zinc sulfate turbidity test), GOT (glutamate-oxaloacetate transaminase), GPT (glutamate-pyruvate transaminase), ALP (alkaline phosphatase), LDH (lactate dehydrogenase), γ-GTP (γ-glutamyl transpeptidase), etc. As well as the method for determining human prolyl 4-hydroxylase by immunoassay previously developed by the present inventors (Japanese Laid-open Patent Appln. No. Sho. 60-204726), therefore, the present invention is very useful in the field of diagnosis of hepatic diseases, since detection of diseases of this type at an early stage can be expected by the measurement of the human type III, IV and VI collagen peptide levels in blood according to the method of this invention and since the diagnosis of fibrosis of hepatic tissues can be made by the method of this invention capable of measuring the human type III, IV and VI collagen peptides. In addition, the method itself of this invention is simple and convenient in the ease of operation and in the use of a smaller amount of samples and a result obtained by the method of this invention is exact and trustworthy. Thus, the method of this invention is extremely useful in the field of diagnosis of hepatic diseases.

BRIEF DESCRIPTION OF THE DRAWINGS

In FIG. 1, the open circles ( - - ) plot the curve for the human type III collagen, the closed circles ( - - ) for the human type IV collagen, and the solid triangles ( - - ) for the human type VI collagen.

In FIG. 2, the inset solid bar means an average value, the asterisk ( * ) a statistical significance ( $P<0.01$ ) of the average when the serum concentration of the human type III collagen peptide is compared between normal subjects and patients. Each numeral in parentheses means the number of samples and the shaded part means a mean of the normal subjects (M)±2SD.

In FIG. 3, the inset solid bar means an average value. The double asterisk ( ** ) means a statistical significance ( $P<0.001$ ) of the average when the serum concentration of the human type IV collagen peptide is compared between the normal subjects and the patients. Each numeral in the parentheses means the number of samples and the shaded part means a lean of the normal subjects (M)-±2SD.

In FIG. 4, the inset solid bar means an average value. The asterisk ( * ) means a statistical significance ( $P<0.05$ ) of the average when the serum concentration of the human type VI collagen peptide is compared between the normal subjects and the patients. Each numeral in parentheses means the number of samples and the shaded part means a mean of the normal subject (M)-±2SD.

PREFERABLE EMBODIMENTS OF THE INVENTION

Figure 1:
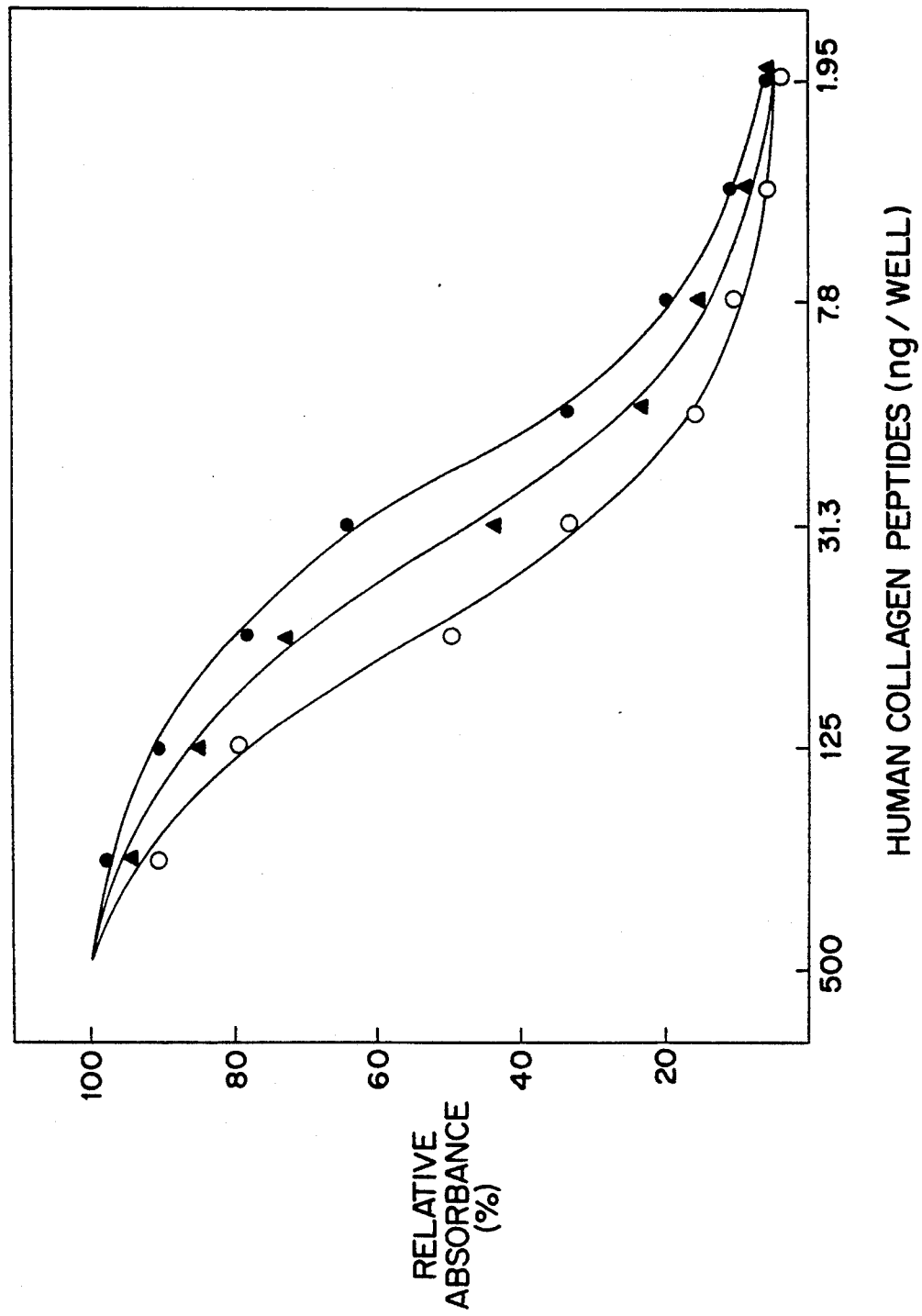
FIG. 1 shows a standard curve of each human collagen peptide based on the sandwich technique using the purified mouse anti-human collagen peptide monoclonal antibody (IgG type) and the purified rabbit anti-human collagen peptide polyclonal antibody.

The present invention will now be illustrated in more detail by way of the following examples, but it is to be construed that the scope of this invention is not limited by these specific examples.

EXAMPLE 1

Preparation of Monoclonal Antibodies to Human Collagen Peptides (a) Purification of human type III, IV and VI collagens as antigen:

According to the method of Mayne et al. [Artery, 7, 262–280, (1980)], human placenta was homogenized in 0.5-N acetic acid, digested with pepsin (1 mg/ml) to make the contained collagens soluble, and incorporated with NaCl so that its final concentration became 2-M to effect precipitation of the collagens. The precipitate was dissolved in 0.5-N acetic acid from which a fraction containing the type I and III collagens was obtained through dialysis against a 0.5-N acetic acid solution containing 0.7-M NaCl and the supernatant was then dialyzed against a 0.5-N acetic acid solution containing 1.2-M NaCl whereby a fraction containing the type IV and V collagens was precipitated. Further, the supernatant was dialyzed against a 0.5-N acetic acid solution containing 1.8-M NaCl to precipitate the type VI collagen. The fraction containing the type I and III collagens obtained above was dissolved in a 50-mM tris-HCl buffer solution (pH 7.4) containing 0.5-M NaCl and dialyzed sequentially against a 50-mM tris-HCl buffer solution (pH 7.4) containing 1.7-M NaCl and a tris-HCl buffer solution (pH 7.4) containing 2.7-M NaCl whereby the type III and I collagens were precipitated, respectively, and the type III collagen was separated from the type I collagen. In the same manner as described for the type I and III collagens, the fraction containing the type IV and V collagens was dissolved in a 50-mM tris-HCl buffer solution (pH 7.4) containing 0.5-M NaCl and dialyzed against a 50-mM tris-HCl buffer solution (pH 7.4) containing 2.2-M NaCl whereby the type IV collagen was precipitated and separated from the type V collagen. The quality of the type III, IV and VI collagens thus obtained was examined according to Sykes et al. method reported in Biochem. Biophys. Res. Commun., 72, 1472-1480 (1976) by subjecting these collagens to the sodium dodecyl sulfate-polyacrylamide gel electrophoresis (SDS-PAGE) whereby the purity of these collagens was respectively determined as about 95%.

(b) Preparation of antibody-producing cells:

Two 8 weeks old BALB/c female mice were initially injected intraperitoneally with 100 μg of each of the human type III, IV and VI collagens in Freund's complete adjuvant. After the initial administration, the mice were then forced to receive a booster injection of 100 μg antigen dissolved in a 50-mM tris-HCl buffer solution (pH 7.4) containing 0.5-M NaCl, 2 to 4 times at 2 to 4 week intervals. As a final immunization, the mice were subjected to subsidiary immunization by intravenous administration. After 3 days, the mice were killed to extirpate their spleens and the splenocytes were harvested.

(c) Cell fusion:

Materials and methods used are as follows:

RPMI 1640 culture medium: RPMI No. 1640 (Difco Lab.) incorporated with sodium bicarbonate (12 mM), sodium pyruvate (1 mM), L-glutamine (2 mM), penicillin G potassium (50 u/ml), streptomycin sulfate (50 μg/ml) and amikacin sulfate (100 μg/ml), adjusted at pH 7.2 with dry ice and filtered through a 0.2 μm Toyo membrane filter for sterilization.

NS-1 culture medium: the above RPMI 1640 culture medium incorporated with 15% (v/v) fetal bovine serum (M.A. Bioproducts) sterilely filtered.

HAT selection medium: the above NS-1 culture medium further incorporated with hypoxanthine (100 μM), aminopterine (0.4 μM) and thymidine (16 μM).

HT culture medium: the same medium as the above HAT with the exception of aminopterine.

PEG 4000 solution: RPMI 1640 culture medium without calf serum, containing 50% (w/w) polyethylene glycol (PEG 4000, Merck).

Utilizing 8-azaguanine-resistant myeloma cell line, NS-1 (P3-NS1-1), cell fusion was effected according to a slightly modified method of Oi and Herzenberg described in "Selected Method in Cellular Immunology" (ed. B. B. Mishell and S. M. Shiigi, W. H. Freeman and Company, (1980), pp. 351-372). The karyo-splenocytes produced as described in the preceding (b) (cell viability 95%) were mixed in a ratio of 5 or 6 to 1 with mouse myeloma cells (cell viability 95%) for fusion. Thus, the splenocytes and the myeloma cells were respectively washed in RPMI 1640 culture medium, suspended in the same medium and mixed together for fusion in the ratio described above. 40 ml of the RPMI 1640 culture medium was put into a 50 ml conical styrene resin test tube (Iwaki Glass, Japan), centrifuged at 400 xg for 10 min., and the supernatant was discarded completely by suction. To the precipitated cells was added dropwise in 1 min. 1 ml of the PEG 4000 solution warmed at 37° C. with gentle stirring. The cells were resuspended and dispersed by stirring gently for another minute. To the suspension was then added dropwise in 1 min. 1 ml of the RPMI 1640 culture medium warmed at 37° C. After repeating the same operation once more, the cells were dispersed again, by adding the same culture medium dropwise in 2 to 3 min. under continuous agitation. The dispersion was centrifuged at 400 xg for 10 min., and the supernatant was removed completely by suction. To the precipitated cells was added rapidly 10 ml of the NS-1 culture medium warmed at 37° C., and big cell clumps were then dispersed by pipetting carefully with a 10 ml pipette. The dispersion was diluted with 20 ml of the same culture medium, and distributed into 96-well microplates made of polystyrene (Iwaki Glass) so that $5.9 \times 10^5$ cells/0.1 ml of the culture medium might exist in each well. As a preliminary treatment, the 96-well microplates had been treated with 0.2 ml of the NS-1 culture medium overnight at 37° C. in a $CO_2$ incubator, and the culture medium had been removed therefrom by suction on actual use. After completion of the cell fusion, the microplates were incubated at 37° C. in 7% $CO_2$/93% air under saturated humidity.

(d) Selective proliferation of hybridomas by the aid of a selective culture medium:

On the first day of incubation, two drops (ca. 0.1 ml) of the HAT culture medium were added with a Pasteur pipette. On the 2nd, 3rd, 5th, 8th and 11th days, the half (0.1 ml) of each culture medium was replaced with new HAT culture medium. On 14th day, each culture was replaced with HT culture medium. Thereafter, the same procedure was repeated at 3 to 4 day intervals. Usually, sufficient growth of hybridoma cells was observed 2 to 3 weeks after the incubation period. All the wells containing hybridomas were tested for the presence of antibody, using a solid phase-antibody binding test (ELISA) as described in the subsequent (e). All the cultures positive for antibody production were transferred to 24-well plates made of polystyrene (Iwaki Glass) containing 1 ml of the HT culture medium containing $10^7$ mouse thymocytes as feeders. The cultures thus treated were incubated, as described in the preceding (c), at 37° C. in 7% $CO_2$ for about a week. Once or twice during the incubation period 0.5 ml of the supernatant of each well was replaced with 0.5 ml of new HT culture medium. At the time the sufficient growth of hybridomas was observed, the cultures were screened again for the positivity of antibody production by ELISA method, and subjected to a cloning procedure by the limiting dilution method as explained in (f) below. The residual culture after cloning was transferred into a 25 cm³ tissue culture flask made of polystyrene (Iwaki Glass), for the preparation of a frozen sample.

(e) Detection of hybridomas capable of producing anti-human collagen peptide by means of the solid phase-antibody binding test (ELISA):

A method used for the present example was a slight modification of the method of Rennard et al. described in Anal. Biochem., 104, 205-214, (1980) which is appropriate for the detection of antibody production in hybridoma. Each well of 96-well microtitration plates (Flow Lab.) was coated with 0.5-1.0 μg of the human type III, IV or VI collagen, and the wells remained uncoated were blocked with 1% bovine serum albumin (BSA). To the wells was added a part of the supernatant from the wells exhibiting hybridoma growth. The incubation was carried out at room temperature for about 1 hr. After the addition of goat anti-mouse immunoglobulin (Cappel Lab.) labelled with horseradish peroxidase as a secondary antibody, further incubation was carried out at room temperature for about 1 hr. The brown color produced by the addition of $H_2O_2$ and o-phenylenediamine as a substrate was recognized qualitatively by naked eyes or measured by way of spectrophotometry for absorbance at 500 nm using a Corona double wave microplate spectrophotometer (MTP-22, Corona Electric).

(f) Cloning:

In order to obtain hybridomas capable of producing monoclonal antibodies it is necessary for cloning to treat cultures according to the limiting dilution method, since each well can develop more than two kinds of hybridomas. A cloning culture medium containing in the NS-1 culture medium $10^7$ feeder cells per ml prepared from mouse thymocytes was prepared and placed in the three groups of 36, 36 and 24 wells of a 96-well microwell, with 5, 1 and 0.5 hybridomas being added to the wells of the three groups, respectively. About 0.1 ml of the NS-1 culture medium was added to each well on the 5th and 12th day after incubation. About 14 to 15 days after the cloning when the sufficient growth of hybridoma could be recognized, the culture group in which more than 50% wells showed no colony formation was submitted to ELISA. When all of the tested wells showed positivity for antibody production, the colonies in antibody-positive wells were enumerated and out of them 4-6 wells exhibiting the formation of one colony were selected for recloning. Finally, 5, 22 and 5 clones were obtained for the type III, IV and VI collagens.

(g) Production in vitro and in vivo of monoclonal antibody:

Monoclonal antibodies can be obtained from the supernatant of a proper culture medium such as NS-1 culture medium in which the clones are incubated (in vitro proliferation) (The concentration of the monoclonal antibody protein 10–100 μg/ml). In case a large amount of antibody is needed, on the other hand, it is recommended to adopt an in vivo proliferation as described below. A carcinogenic excitant, Pristane (2,6,10,14-tetramethylpentadecane, Aldrich Chemical), was administered to animals (BALB/c) intraperitoneally in an amount of 0.5 ml per animal, which were of the same strain as those providing the Splenocytes and the myeloma cells. One to 3 weeks after the administration, $1 \times 10^7$ cells of hybridoma were administered intraperitoneally as above, and ascites containing monoclonal antibody protein in a concentration of 4–7 mg/ml were obtained after 1 to 2 weeks.

(h) Isotypes of monoclonal antibodies with heavy and light chains:

First of all, each of the resultant ascites was dispersed into a well coated with the human type III, IV or VI collagen for binding according to the above-described ELISA method. After washing the well, different subclass specific rabbit anti-mouse Ig antibodies (Zymed Lab.) were added thereto. After washing the well, affinity purified goat anti-rabbit IgG ( H+L ) antibody labeled with horseradish peroxidase, was added thereto, and 2,2'-azino-di(3-ethylbenzthiazoline sulfate-6) as a substrate and hydrogen peroxide were then added to detect the resultant monoclonal antibodies. The results are shown in Tables 1, 2 and 3. Among the resultant monoclonal antibodies against the human type III collagen, four antibodies contain immunoglobulin chain $\gamma1/\kappa$ and one antibody contains $\gamma2a/\kappa$ (Table 1). Among those against the human type IV collagen, sixteen antibodies contain $\gamma1/\kappa$, two antibodies $\gamma2b/\kappa$, one antibody $\alpha/\kappa$ and three antibodies $\mu/\kappa$ (Table 2). Among those against the human type VI collagen one antibody contains $\gamma1/\kappa$, another one antibody $\gamma2a/\kappa$ and three antibodies $\gamma2b/\kappa$ (Table 3).

(i) Purification of monoclonal antibody:

Each of the ascites obtained in the foregoing (g), was fractionated with ammonium sulfate (40% saturation) and IgG class was subjected to chromatography on DEAE Sephacel (Pharmacia) equilibrated with a 40-mM phosphate buffer solution (pH 8.0) containing 0.06-M NaCl to separate an unabsorbed fraction. This IgG fraction was gel-filtered on Sephacryl S-300 superfine column (Pharmacia) equilibrated with a 50-mM phosphate buffer solution (pH 7.4) containing 0.42-M NaCl, whereby the fetal calf serum and a mouse-derived protein contained therein were separated and removed. In the purification of IgA and IgM fractions, these fractions were obtained separately by elution with a NaCl solution of 0.06–1.0M gradient on DEAE-Sephacel column chromatography. The subsequent gel-filtration was carried out under the same condition as used for the IgG class.

EXAMPLE 2

Preparation of Antisera and Polyclonal Antibodies Against the Human Type III, IV and VI Collagens Rabbits were immunized, being injected subcutaneously 4–6 times at an interval of 2 weeks with 1 mg of each of the human type III, IV and VI collagens which had been purified from human placenta in the same manner as described in Example 1(a), together with equivalent Freund's complete adjuvant. The antisera obtained as final product were purified by affinity chromatography using a column coupled with each type of the human collagens. In order to assess the antibody titer and the specificity of immunizing activity, the polyclonal antibodies were examined for cross-reaction with each type of the human collagens according to ELISA method referred to in Example 1(e). The result proved that the polyclonal antibodies were highly specific; the polyclonal antibodies were cross-reacted only with the corresponding type of the human collagens.

EXAMPLE 3

Figure 2:
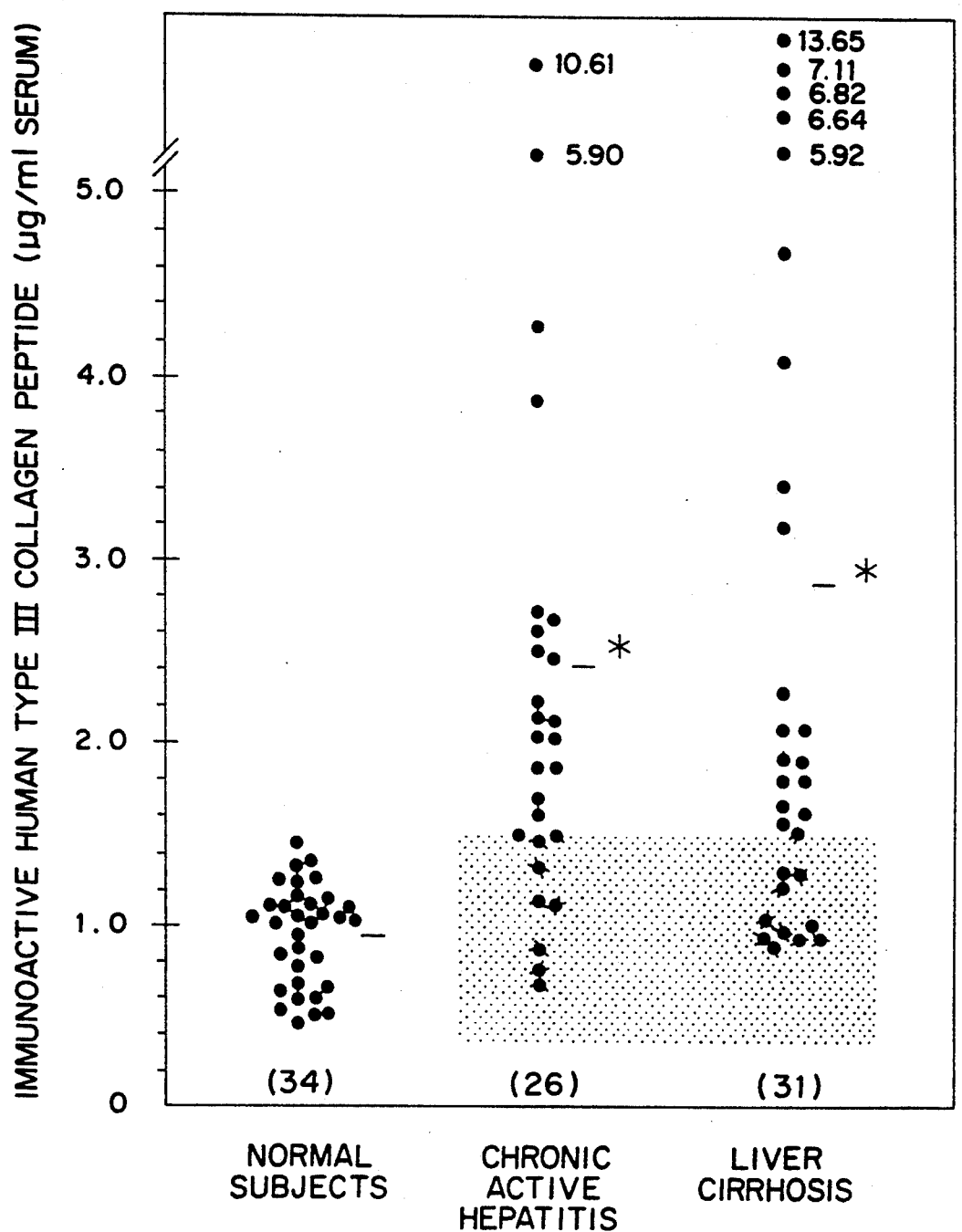
FIG. 2 shows a serum level of immunoactive human type III collagen peptide in normal subjects and in patients with chronic active hepatitis and liver cirrhosis.
Figure 3:
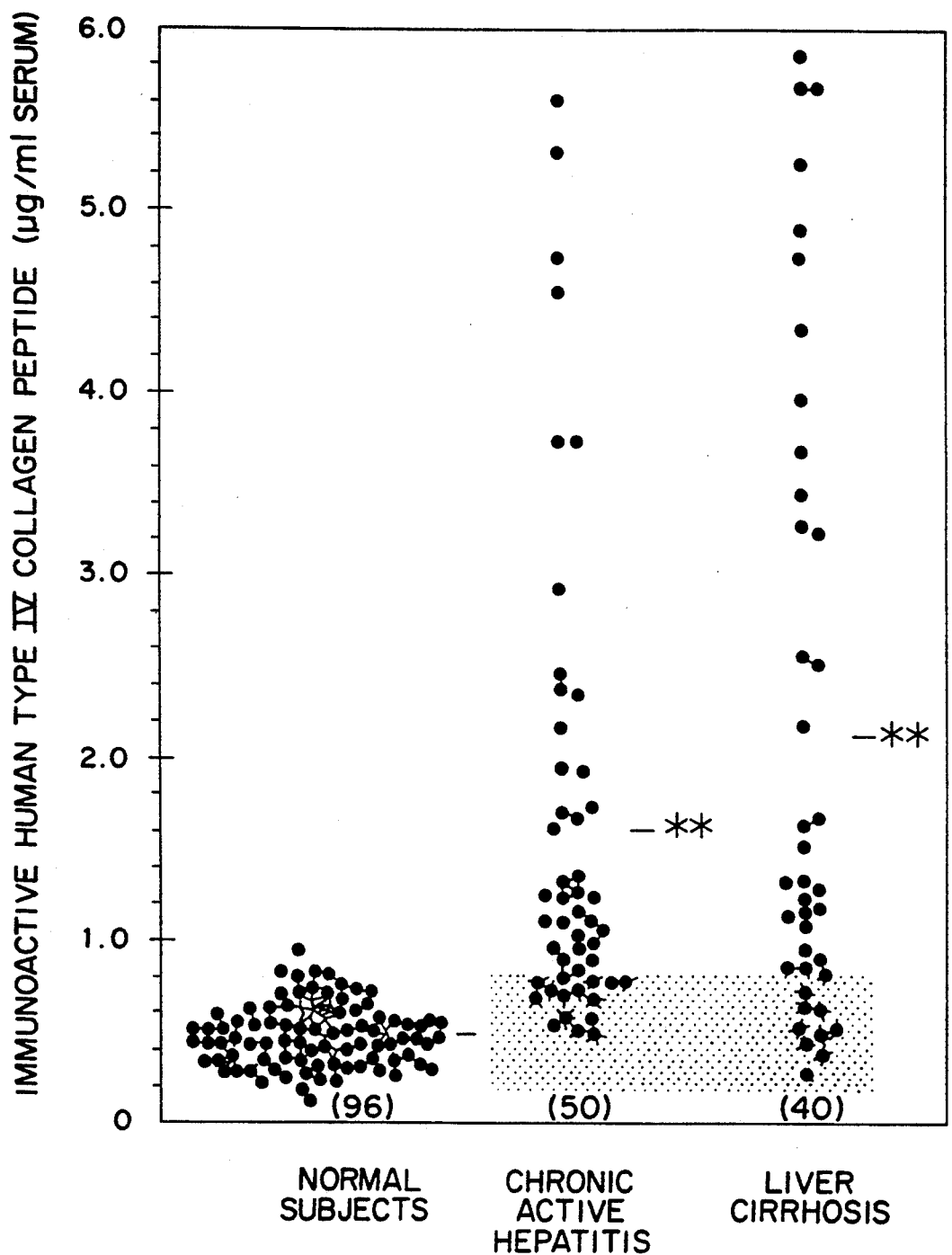
FIG. 3 shows a serum level of immunoactive human type IV collagen peptide in normal subjects and in patients with chronic active hepatitis and liver cirrhosis.
Figure 4:
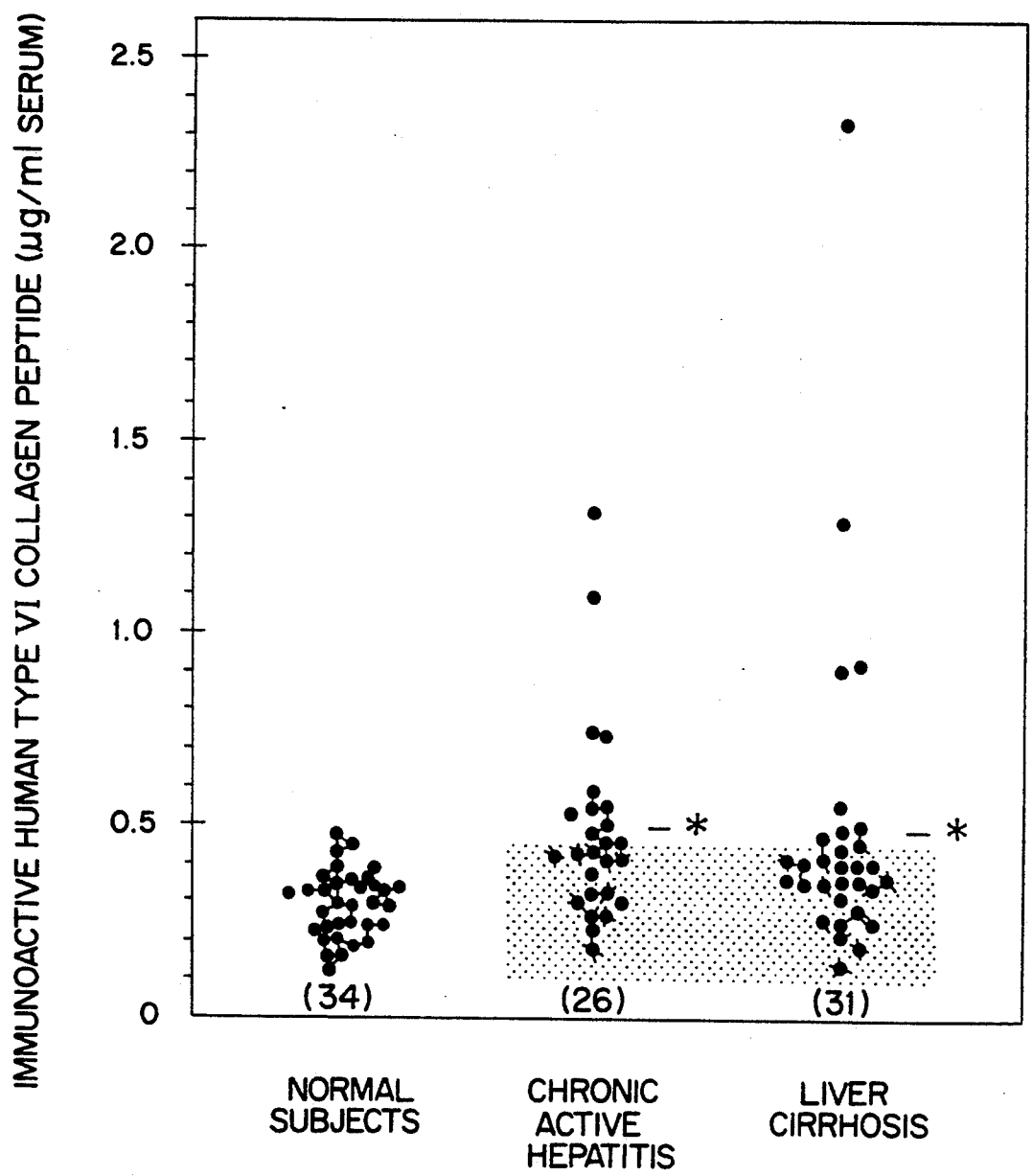
FIG. 4 shows a serum level of immunoactive human type VI collagen peptide in normal subjects and in patients with chronic active hepatitis and liver cirrhosis.

Measurement of the Human Type III, IV and VI Collagen Peptides in Serum By Using a Combination of the Monoclonal and Polyclonal Antibodies The type III, IV and VI collagens in human serum were assayed using a sandwich method as described in "Enzyme immunoassay" (eds., E. Ishikawa, T. Kawai and K. Miyai, Igakushoin, 2nd ed. (1982), pp. 30–49). Polystyrene 96-well microtitration plates (Flow Lab.) were coated with the monoclonal antibodies to the human type III, IV or VI collagen obtained in a purified form in Example 1(i), and the others were blocked with 1.0% BSA. On the other hand, the purified human type III, IV or VI collagen obtained in Example 1(a) was used as a standard, and 10 μl of each of the sera collected from normal subjects and from patients with chronic active hepatitis or liver cirrhosis which was definitely diagnosed based on histological observation of the tissue biopsied was used as a human serum sample. The sample solutions were added to the microtitration plates treated with the monoclonal antibodies and incubated at room temperature for 1 hour. After the addition of the rabbit polyclonal antibodies obtained in Example 2 and with goat anti-rabbit IgG (Miles-Yeda) labeled with horseradish peroxidase as a secondary antibody, the samples were incubated at room temperature for about 1 hour. After the subsequent addition of hydrogen peroxide and o-phenylenediamine as a substrate, the absorbance of the brownish red reaction product formed was measured using a Corona double wavelength microplate spectrophotometer (MTP-22). The standard curves for the human type III, IV and VI collagens were drawn in FIG. 1, from which it was read out that the sensitivity was ca. 5 ng for all the human type collagens examined. According to this sandwich method enabling the assay of collagen peptide concentration in blood, it is recognized that the concentration in blood was significantly increased in case of hepatic diseases (FIGS. 2, 3 and 4). The concentration of the type III and IV collagen peptides was increased especially in blood from patients with chronic active hepatitis and liver cirrhosis. In this Example, the present invention is mainly explained with respect to the sandwich method which utilizes the monoclonal antibody as a solid phase, and the peroxidase-labeled anti-rabbit IgG as a secondary antibody. However, the present invention is also applicable as a means for determining blood collagen peptides to the sandwich immunoassay wherein an enzyme-labeled mouse monoclonal antibody or rabbit polyclonal antibody (IgG and Fab') to the human type III, IV and VI collagen peptides is used, as described by Yoshitake in "Men-eki Jikken Sosa-ho (Manual for Immunological Experiments)" vol. XI (1982), pp. 3497–3519, and also to the radioimmunoassay disclosed in Japanese Laid-open Patent Appln. No. Sho. 61-202162 and Japanese Patent Appln. No. Sho. 60-179357 wherein isotope-labeled monoclonal and polyclonal antibodies are used.

EXAMPLE 4

Measurement of the Human Type III Collagen Peptide in Serum By the Aid of Monoclonal Antibody The measurement was carried out according to the method of Ishikawa et al., J. Immunoassay 4, 209–327 (1983) wherein the monoclonal antibody was used for a dual function as a solid phase and a conjugate. At first, the purified monoclonal antibody IgG1 (clone No. 12) to the human type III collagen, which had been obtained in Example 1(i), was dissolved in a 0.1-M phosphate buffer solution (pH 7.5) containing 0.1% sodium azide, and adjusted at 0.1 mg/ml in concentration. A polystyrene ball (6.5 mm in diameter, Precision Plastic Ball Co.) as a solid phase was soaked in the solution and coated with the antibody. After collecting the solution used for the soaking, the polystyrene ball was washed with a 10-mM phosphate buffer solution (pH 7.0) containing 0.1% BSA, 0.1M NaCl and 0.1% sodium azide, to be ready for use. On the other hand, the purified human type III collagen obtained in Example 1(a) was used as a standard sample and a 10 μl of each serum from healthy subjects and from patients with chronic active hepatitis and liver cirrhosis which had been definitely diagnosed according to the histological observation of the tissue biopsied was used as a serum sample. A solution of these samples was added to the polystyrene ball coated with the monoclonal antibody, and incubated at 30° C. for 1 hour (the first reaction). The solution was then incorporated with the peroxidase-labeled monoclonal antibody IgG (clone No. 53) or the fragment, Fab' derived from clones different from those which provided the monoclonal antibody for the solid phase as a conjugate, and incubated at 30° C. for 1 hour (the second reaction). The solution was then incorporated with hydrogen peroxide and 3,3',5,5'-tetramethylbenzene (TMBZ) as a substrate and incubated for reaction at 30° C. for 1 hour (the third reaction).

This enzyme reaction was then stopped with 1.33-N $H_2SO_4$. After the reaction has ceased, the absorbance of the reaction product was measured at 450 nm wave length by means of a microflow ultraviolet-visible spectrophotometer (Shimazu, UV-730), using water as a reference and a difference between the absorbance of the blank and that of the reaction products was calculated. From the referential absorbance curve obtained from the standard samples, the content of the type III collagen peptide in 10 μl of the serum sample was read out, and multiplied by 100 to estimate the amount of the type III collagen contained in 1 ml of the serum sample.

EXAMPLE 5

The Measurement of the Human Type IV Collagen in Serum By the Aid of the Monoclonal Antibody The condition for measurement was identical with that for the human type III collagen peptide in serum described in Example 4, except that the monoclonal antibody IgG1 (clone 4H12, accession no. FERM BP-2847) was used as a solid phase and the monoclonal antibody IgG or Fab'(clone 1D3, accession no. FERM BP-2846) labeled with a peroxidase was used as a conjugate (These cell lines were deposited with The Fermentation Research Institute Agency of Industrial Science and Technology having the address 1-3, Higashi 1-chome, Tsukuba-shi, Ibaraki-ken, 305, Japan). Thus, the assessment of serum type IV collagen peptide was undertaken, using sera from normal subjects and patients with chronic active hepatitis and liver cirrhosis.

TABLE 1

| Monoclonal antibody | Isotype | Chain |
|---|---|---|
| No. 11 | IgG2a | γ2a/κ |
| No. 12 | IgG1 | γ1/κ |
| No. 33 | IgG1 | γ1/κ |
| No. 41 | IgG1 | γ1/κ |
| No. 53 | IgG1 | γ1/κ |

TABLE 2

| Monoclonal antibody | Isotype | Chain |
|---|---|---|
| 4C1 | IgM | μ/κ |
| 7A11 | IgM | μ/κ |
| 1D3 | IgG1 | γ1/κ |
| 1D6 | IgG1 | γ1/κ |
| 1E10 | IgG1 | γ1/κ |
| 2A7 | IgM | μ/κ |
| 2D5 | IgG1 | γ1/κ |
| 2H1 | IgA | α/κ |
| 3A9 | IgG1 | γ1/κ |
| 4B1 | IgG1 | γ1/κ |
| 4H12 | IgG1 | γ1/κ |
| 5D10 | IgG1 | γ1/κ |
| 5F6 | IgG1 | γ1/κ |
| 6B5 | IgG1 | γ1/κ |
| 6C11 | IgG1 | γ1/κ |

TABLE 2-continued

| Monoclonal antibody | Isotype | Chain |
|---|---|---|
| 6G5 | IgG2b | γ2b/κ |
| 7C8 | IgG1 | γ1/κ |
| 7H2 | IgG1 | γ1/κ |
| 8B4 | IgG1 | γ1/κ |
| 8G12 | IgG1 | γ1/κ |
| 9A3 | IgG2b | γ2b/κ |
| 9C7 | IgG1 | γ1/κ |

TABLE 3

| Monoclonal antibody | Isotype | Chain |
|---|---|---|
| No. 14 | IgG2b | γ2b/κ |
| No. 17 | IgG2b | γ2b/κ |
| No. 26 | IgG1 | γ1/κ |
| No. 29 | IgG2b | γ2b/κ |
| No. 38 | IgG2a | γ2a/κ |

What is claimed is:

1. A method for determining human type IV collagen peptides by way of enzyme sandwich immunoassay which comprises:

(a) contacting a serum sample suspected of containing human type IV collagen peptides with a first monoclonal antibody, which is produced by a hybridoma having all of the identifying characteristics of the hybridoma deposited as FERM BP-2847, specific for human type IV collagen peptides, said first monoclonal antibody being bound to a solid phase, under conditions which allow formation of a first reaction product between said first monoclonal antibody and said type IV collagen peptides;

(b) contacting a second monoclonal antibody, which is produced by a hybridoma having all of the identifying characteristics of the hybridoma deposited as FERM BP-2846, specific for said human type IV collagen peptides and which is conjugated with an enzyme, under conditions which allow formation of a second reaction product between said second monoclonal antibody and said first reaction product;

(c) adding a substrate for said enzyme;

(d) assaying for said enzyme reaction products of said substrate; and (e) relating the presence of said enzyme reaction products to the presence of human type IV collagen peptides in said serum sample.

2. A method of detecting a liver disorder, which comprises measuring the presence of human type IV collagen peptides in serum from a host suspected of having a liver disorder using the method of claim 1.

3. The method according to claim 2, wherein the liver disorder is chronic active hepatitis.

* * * * *